US009834570B2

(12) United States Patent
Sudalai et al.

(10) Patent No.: US 9,834,570 B2
(45) Date of Patent: Dec. 5, 2017

(54) ONE STEP PROCESS FOR REGIOSELECTIVE SYNTHESIS OF α-ACYLOXY CARBONYLS

(71) Applicant: COUNCIL OF SCIENTIFIC AND INDUSTRIAL RESEARCH, New Delhi (IN)

(72) Inventors: Arumugam Sudalai, Pune (IN); Rambabu Reddi, Pune (IN); Pushpa Malekar, Pune (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/895,442

(22) PCT Filed: Jun. 3, 2014

(86) PCT No.: PCT/IN2014/000374

§ 371 (c)(1),
(2) Date: Dec. 2, 2015

(87) PCT Pub. No.: WO2014/195972

PCT Pub. Date: Dec. 11, 2014

(65) Prior Publication Data

US 2016/0115182 A1 Apr. 28, 2016

(30) Foreign Application Priority Data

Jun. 3, 2013 (IN) ........................... 1661/DEL/2013

(51) Int. Cl.

| | |
|---|---|
| ***C07D 213/46*** | (2006.01) |
| ***C07C 69/76*** | (2006.01) |
| ***C07F 7/18*** | (2006.01) |
| ***C07C 67/39*** | (2006.01) |
| ***C07D 213/803*** | (2006.01) |
| ***C07C 205/57*** | (2006.01) |
| ***C07D 307/60*** | (2006.01) |
| ***C07D 309/30*** | (2006.01) |

(52) U.S. Cl.
CPC ............ *C07F 7/1844* (2013.01); *C07C 67/39* (2013.01); *C07C 205/57* (2013.01); *C07D 213/803* (2013.01); *C07D 307/60* (2013.01); *C07D 309/30* (2013.01)

(58) Field of Classification Search
CPC .............................. C07D 213/46; C07C 69/76
USPC ................................. 546/318, 322; 560/106
See application file for complete search history.

(56) References Cited

U.S. PATENT DOCUMENTS

| | | | |
|---|---|---|---|
| 5,084,584 | A | 1/1992 | Wantanabe et al. |
| 6,384,265 | B1 | 5/2002 | Shi |
| 8,143,423 | B2 | 3/2012 | Zhang et al. |
| 2003/0083376 | A1 | 5/2003 | Eh |

OTHER PUBLICATIONS

Reddi, R.N. et al.: N-heterocyclic carbene catalyzed regioselective oxo-acyloxylation of alkenes with aromatic aldehydes: a high yield synthesis of alpha-acyloxy ketones and esters. Organic & Biomolec. Chem., vol. 11, pp. 6477-6482, 2013.*

International Search Report and Written Opinion for International Application No. PCT/IN2014/000374, dated on Nov. 17, 2014.

Dirocco, Daniel A., et al., Organocatalystic Hydroacylation of Unactivated Alkenes, Agewandte Chemie International Edition, vol. 50, No. 35, Jun. 30, 2011, pp. 7982-7983.

Li, Yi., et al., NHCs-mediated benzoates formation directly from aromatic aldehydes and alkyl halides, Tetrahedron, Mar. 5, 2012, pp. 3611-3615.

Enders, Dieter., et al. Organocatalysis by N-Heterocyclic Carbenes, Chemical Reviews, vol. 107, No. 12, Dec. 1, 2007, pp. 5606-5655.

Levene, P.A., et al., Acetol, Organic Syntheses, Coll. vol. 2, p. 5, 1943.

* cited by examiner

*Primary Examiner* — Charanjit Aulakh
(74) *Attorney, Agent, or Firm* — Andrews Kurth Kenyon LLP

(57) ABSTRACT

A regioselective N-Heterocyclic Carbene (NHC) catalyzed one step process for high yield synthesis of α-acyloxy carbonyl compounds is disclosed.

Scheme 1

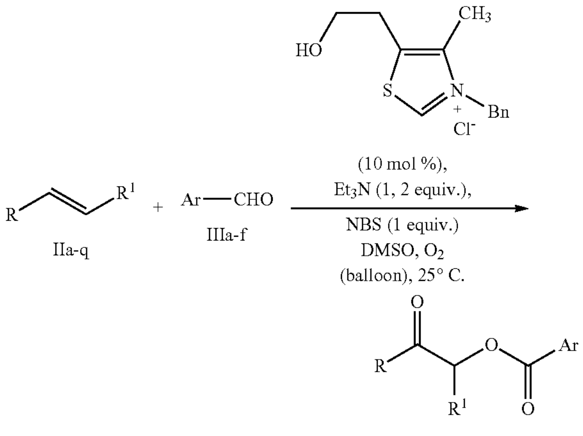

IIa-q IIIa-f Ia-v

7 Claims, 1 Drawing Sheet

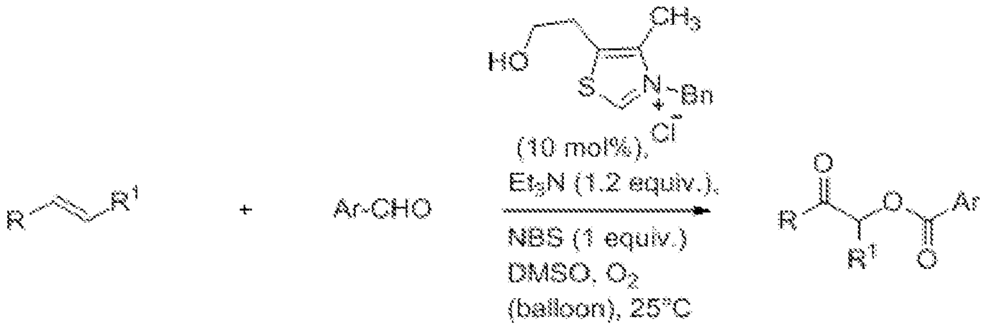
IIa- q IIIa-f Ia-v

ONE STEP PROCESS FOR REGIOSELECTIVE SYNTHESIS OF α-ACYLOXY CARBONYLS

CROSS-REFERENCE TO RELATED APPLICATIONS

This application is a U.S. National Stage Application under 35 U.S.C. §371 of International PCT Patent Application Serial No. PCT/IN2014/000374 filed on Jun. 3, 2014, which claims priority to Indian Patent Application Serial No. 1661/DEL2013, filed on Jun. 3, 2013, the entire disclosures of which are hereby incorporated herein by reference in their entireties for all purposes.

FIELD OF THE INVENTION

The present invention relates to a regioselective one step process for synthesis of α-acyloxy carbonyl compounds. Particularly, present invention discloses a regioselective one step process for synthesis of α-acyloxy carbonyl compounds from alkenes.

BACKGROUND AND PRIOR ART OF THE INVENTION

α-acyloxy carbonyls are often found as the key structural motif for many natural products with interesting biological activities and synthetic therapeutics, refer. P. A. Levene, A. Walti, Org. Synth. Coll. Vol. II 1943, 5. These compounds are the potential starting materials for the pfitzinzer reaction in the synthesis of quinoline salicylic acids and their further functionalization results in various biologically active natural products. The acyl groups can serve as useful protecting groups for the hydroxyl functions in α-hydroxy carbonyls. Their importance is reflected in the extensive synthetic research directed toward introducing acyloxy group in a chemo, regio, stereo and enantioselective manner.

U.S. Pat. No. 6,384,265 discloses method for stereoselectively producing an alpha-acyloxy carbonyl compound from an enol ester epoxide comprising contacting the enol ester epoxide With a chiral acid catalyst under conditions sufficient to stereoselectively produce the alpha-acyloxy carbonyl compound With inversion of stereochemistry.

US 2003/0083376 discloses depot preparations comprising at least one compound of the formula given below.

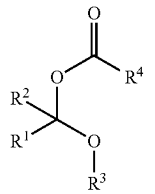

in which R1, R3 and R4, independently of one another, are an organic radical having 1 to 30 carbon atoms; R2 is hydrogen or an organic radical having 1 to 30 carbon atoms, and the compound of the formula given above, after hydrolysis or enzymatic cleavage, releases an alcohol and a carboxylic acid in addition to the aldehyde or ketone.

U.S. Pat. No. 5,084,584 discloses a process for producing an a-acyloxy-a, β unsaturated carbonyl comprising bringing a propargyl ester into contact with a platinum group metal compound catalyst in the presence of oxygen and/or a peroxide.

U.S. Pat. No. 8,143,423 discloses a process for preparing hydroxamic acids. The process comprises reacting an aldehyde with a nitroso compound in the presence of a N-heterocyclic carbene (NHC) catalyst.

Prior art processes for synthesis of α-acyloxy carbonyls are catalysed by metals, including the direct oxidative coupling of carbonyl compounds with toxic heavy metal oxidants namely $Pb(OAc)_4$, $Tl(OAc)_3$, $Mn(OAc)_3$, thus providing environmentally unfriendly processes.

Some processes replaced heavy metal salts with stoichiometric use of N-methyl-Oacylhydroxylamines, but preparation of N-methyl-Oacylhydroxylamines is not an easy process, Also, this is needed in stoichiometric quantities to lead to the desired α-acyloxy carbonyls. Other prior art processes use harsh conditions for synthesis of desired compounds, making them both economically and environmentally non friendly. Some reports indicate the use of halo substituted carbonyls ie α-halo carbonyls as tarting materials, which are not commercially available, and therefore will have to be synthesized. This results in long evolving methods of synthesis of desired compounds.

Thus there is a need in the art to provide a simple, environmentally friendly process for synthesis of α-acyloxy carbonyls, such that the process provides a high degree of regio selectivity.

OBJECTS OF THE INVENTION

Main objective of the present invention is to provide a one step, one pot process for synthesis of α-acyloxy carbonyls.

Another objective of the invention is to provide a one step, one pot process for synthesis of α-acyloxy carbonyls with high degree of regio selectivity.

Yet another objective of the present invention is to provide an environmentally friendly process conducted in mild conditions with easily available starting compounds.

BRIEF DESCRIPTION OF THE DRAWING

FIG. 1 represents NFIC catalyzed oxidative functionalization of alkenes with aldehydes for synthesis of α-acyloxy carbonyls.

SUMMARY OF THE INVENTION

Accordingly, present invention provides a single-step, one pot process for preparation of α-acyloxy carbonyl compound of general formula (I)

General formula (I)

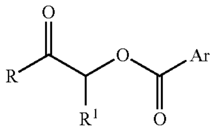

wherein R is selected from H, alkyl, aryl, Bn; $R^1$ is selected from H, alkyl, substituted aryl, unsubstituted aryl —$CH_2$OTBS (TBS=Tertiary butyl silyl), —$CH_2$OBn, —OR, OMOM (Methoxy methelene); Ar is selected from substituted aromatic, unsubstituted aromatic or heteroaromatic; R and R1 optionally can combine to form a ring structure;

comprising the steps of:

i. reacting alkene of formula (III) with an aldehyde of formula (IV)

(II)

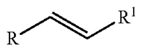

(III)

Ar—CHO in the presence of a N-Heterocyclic carbene catalyst (NHC), a halogen source, tri-ethyl amine and a solvent in oxygen atmosphere at a temperature in the range of 15-30° C. by stirring for period in the range of 10-50 hours to obtain compound of general formula (I);

wherein R is selected from H, alkyl, aryl, Bn; $R^1$ is selected from H, alkyl, substituted aryl, unsubstituted aryl —$CH_2$OTBS (TBS=Tertiary butyl silyl), —$CH_2$OBn, —OR, OMOM (Methoxy methelene); Ar is selected from substituted aromatic, unsubstituted aromatic or heteroaromatic.

In an embodiment of the present invention, N-Heterocyclic carbene catalyst is selected from the group consisting of IVa-IVf, preferably IVa.

IVa

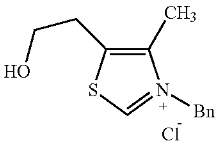

IVb, IVc

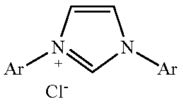

IVd

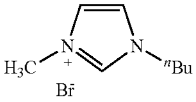

IVe

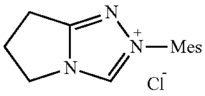

IVf

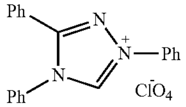

wherein for IVb, Ar=2,4,6-$(CH_3)_3C_6H_2$; for IVc, Ar=2,6-$iPr_2C_6H_3$

In another embodiment of the present invention, halogen source is selected from the group consisting of N-bromo succinamide (NBS), N-iodo succinamide NIS or N-chloro succinamide NCS, preferably NBS.

In yet another embodiment of the present invention, solvent used is di-methyl sulfoxide (DMSO).

In yet another embodiment of the present invention, yield of the compound of general formula 1 is in the range of 70 to 42%.

In yet another embodiment of the present invention, representative compound of general formula I are:

2-Oxo-2-phenylethyl 4-nitrobenzoate (Ia);
2-(4-Methylphenyl)-2-oxoethyl 4-nitrobenzoate (Ib);
2-(4-Bromophenyl)-2-oxoethyl 4-nitrobenzoate (Ic);
2-(4-Fluorophenyl)-2-oxoethyl 4-nitrobenzoate (Id);
2-(4-Acetoxyphenyl)-2-oxoethyl 4-nitrobenzoate (le);
2-(3,4 Dimethoxyphenyl)-2-oxoethyl 4-nitrobenzoate (If);
1-Oxo-2,3-dihydro-1H-inden-2-yl 4-nitrobenzoate (Ig);
2-Oxo-1,2-diphenylethyl 4-nitrobenzoate (Ih);
1-Oxo-1-phenylpropan-2-yl 4-nitrobenzoate (Ii);
3-((Tert-butyldimethylsilyl)oxy)-1-oxo-1-phenylpropan-2-yl 4-nitro benzoate (Ij);
3-(Benzyloxy)-2-oxopropyl 4-nitrobenzoate (Ik);
2-Oxooctyl 4-nitrobenzoate (Il);
2-Oxodecyl 4-nitrobenzoate (Im);
RMD/NEH/CSIR-49
2-Oxo-4-phenylbutyl 4-nitrobenzoate (In);
2-Ethoxy-2-oxoethyl 4-nitrobenzoate (Io);
2-Oxotetrahydro-2H-pyran-3-yl 4-nitrobenzoate (Ip);
2-(Methoxy)-2-oxo-1-phenylethyl 4-nitrobenzoate (Iq);
2-Oxo-2-phenylethyl benzoate (Ir);
2-Oxo-2-phenylethyl 3-methylbenzoate (Is);
2-Oxo-2-phenylethyl 4-bromobenzoate (It);
2-Oxo-2-phenylethyl 4-chlorobenzoate (Iu);
2-Oxo-2-phenylethyl nicotinate (Iv).

DETAILED DESCRIPTION OF THE INVENTION

Present invention provides a one step, one pot process for the synthesis of α-acyloxy carbonyl compounds with regio selectivity, wherein the starting material is an alkene.

The process leads to novel α-acyloxy carbonyl compounds that may be used as key structural motif for synthesis of useful, therapeutically active compounds.

The present invention provides a single-step, one pot process for the preparation of α-acyloxy carbonyl compounds of general formula (I)

GENERAL FORMULA I

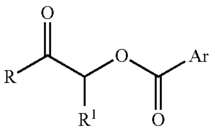

General Formula I
wherein
R=H, alkyl, aryl or Bn; $R^1$=H, alkyl, aryl, —$CH_2$OTBS, —$CH_2$OBn, —OR or OMOM;
Ar=aromatic or heteroaromatic;
comprising reacting alkene of formula (II), with an aldehyde of formula (III)

(II)

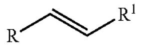

(III)

Ar—CHO wherein, R, R1, Ar are as defined above;
in the presence of a NHC catalyst, a halogen source, triethyl amine and a solvent selected from di-methyl sulfoxide (DMSO) in air at temperature 15-30° C. by stirring for 10-50 hours and isolating compounds of general formula (I) with >70% yields.

N-Heterocyclic carbene catalyst is selected from:

IVa

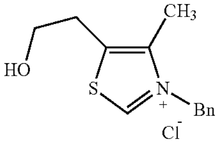

IVb, IVc

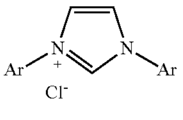

-continued

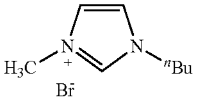

IVd

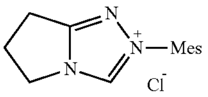

IVe

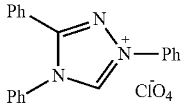

IVf wherein, Vb is Ar=2,4,6-$(CH_3)_3C_6H_2$; Vc is Ar=2,6-$iPr_2C_6H_3$.

Halogen source is selected from N-bromo succinamide (NBS), N-iodo succinamide (NIS) or N-chloro succinamide (NCS) and preferably NBS.

The above process for the preparation of α-acyloxy carbonyl compounds of formula (I), using IVa as NHC— catalyst is depicted below in FIG. 1.

The present invention provides a process with variations of the NHC catalyst IVa-IVf yielding the corresponding α-acyloxy carbonyl starting from styrene and —$NO_2$-benzaldehyde as shown in Table 1.

TABLE 1

NHC catalyzed oxidative functionalization of styrene with 4-$NO_2$-benzaldehyde: Optimization studies

| Entry | NHC catalyst | Base | Solvent | Yield (%)[b] of Ia |
|---|---|---|---|---|
| 1 | IVa | $Et_3N$ | DMSO | 92 (81)[c] (46)[d] |
| 2 | IVb | $Et_3N$ | DMSO | 65 |
| 3 | IVc | $Et_3N$ | DMSO | 47 |
| 4 | IVd | $Et_3N$ | DMSO | 52 |
| 5 | IVe | $Et_3N$ | DMSO | 14 |
| 6 | IVf | $Et_3N$ | DMSO | 8 |

TABLE 1-continued

NHC catalyzed oxidative functionalization of styrene with 4-$NO_2$-benzaldehyde: Optimization studies

| Entry | NHC catalyst | Base | Solvent | Yield (%)[b] of Ia |
|---|---|---|---|---|
| 7 | IVa | NaH | DMSO | 54 |
| 8 | IVa | DBU | DMSO | 52 |
| 9 | IVa | $Cs_2CO_3$ | DMSO | 24 |
| 10 | IVa | $KOBu^t$ | DMSO | 16 |
| 11 | IVa | $Et_3N$ | DMSO (5 eq) + THF | 15 |

[a]Reaction conditions: styrene (5 mmol), p-nitrobenzaldehyde (6 mmol), NHC precatalyst (Va-f) (10 mol %), Base (6 mmol), NBS (5 mmol); all under $O_2$ atmosphere in DMSO, 25° C., 18 h;
[b]isolated yield after column chromatographic purification;
[c]NIS is used instead of NBS;
[d]NCS is used us halogen source.

The present invention provides a process for the preparation of α-acyloxy carbonyl compounds of formula (II), wherein the NHC catalysts is preferably IVa to IVd with yields greater than 50%.

The present invention provides a process with options of aldehydes to provide α-acyloxy carbonyl with high regioselectivity yield greater than 70% as shown in Table 2.

TABLE 2

NHC catalyzed oxidative functionalization of styrene with aromatic aldehydes[a]

| Entry | Aldehydes (IIIa-e) | Time (h) | Products (Ir-v) | Yield (%)[b] of (Ir-v) |
|---|---|---|---|---|
| 1 | benzaldehyde (IIIa) | 38 | Ir | 68 |
| 2 | m-tolualdehyde (IIIb) | 28 | Is | 81 |
| 3 | 4-Br-benzaldehyde (IIIc) | 22 | It | 78 |
| 4 | 4-Cl-benzaldehyde (IIId) | 24 | Iu | 75 |
| 5 | 3-pyridine carboxaldehyde (IIIe) | 22 | Iv | 73 |

[a]Reaction conditions: styrene (5 m · mol), aromaticaldehyde (5.5 mmol), NHC precatalyst Va (10 mol %), $Et_3N$ (5.5 mmol), NBS (5 mmol) in DMSO under $O_2$ atmosphere; 25° C.;
[b]isolated yield after column chromatographic purification.

The present invention provides various α-acyloxy carbonyls synthesized by varying the alkenes (III), with >70% yield as shown in Table 3.

TABLE 3

NHC catalyzed oxidative functionalization of alkenes with 4-$NO_2$-benzaldehyde[a]

| entry | alkenes (IIa-q) | time (h) | products (Ia-q) | yield (%)[b] |
|---|---|---|---|---|
| 1 | styrene (IIa) | 18 | Ia | 92 |
| 2 | 4-$CH_3$-styrene (IIb) | 20 | Ib | 77 |
| 3 | 4-Br-styrene (IIc) | 18 | Ic | 71 |
| 4 | 4-F-styrene (IId) | 22 | Id | 79 |
| 5 | 4-OAc-styrene (IIe) | 23 | Ie | 82 |
| 6 | 3,4-$(OMe)_2$ styrene (IIf) | 26 | If | 74 |
| 7 | indene (IIg) | 18 | Ii | 72 |
| 8 | stilbene (IIh) | 24 | Ij | 81 |
| 9 | Ph—CH═CH—$CH_2$—OTBS (IIi) | 28 | Ig | 92 |
| 10 | 3,4-(O—$CH_2$—O)—Ph—CH═CH—$CH_2$—OTBS (IIj) | 26 | Ih | 81 |
| 11 | benzyloxy 1-propene (IIk) | 27 | Ik | 79 |
| 12 | 1-octene (IIl) | 32 | Il | 71 |
| 13 | 1-decene (IIm) | 29 | Im | 76 |
| 14 | 4-phenyl-1-butene (IIn) | 26 | In | 74 |
| 15 | ethoxyethene (IIo) | 30 | Io | 78[c] |
| 16 | dihydropyran (IIp) | 28 | Ip | 69 |
| 17 | Ph—$CH_2$—CH═CH—$OCH_2OCH_3$ (IIq) | 32 | Iq | 73 |

[a]Reaction conditions: alkene (5 mmol), p-nitrobenzaldehyde (5.5 mmol), NHC precatalyst IVa (10 mol %), $Et_3N$ (5.5 mmol), NBS (5 mmol) in DMSO under $O_2$ atmosphere; 25° C.;
[b]isolated yield after column chromatographic purification;
[c]reaction was carried out at 0° C.

EXAMPLES

Following examples are given by way of illustration therefore should not be construed to limit the scope of the invention.

Example 1

General Experimental Procedure

To a solution of alkenes (IIIa-q) (1 equiv.) in DMSO (20 ml), N-Heterocyclic carbene (10 mol %), N-Bromo succinamide (1 equiv.), triethyl amine (1.2 equiv.) and aldehyde (IVa-f) were added under oxygen atmosphere. The reaction mixture was then stirred at 25° C. After completion (monitored by TLC), the reaction mixture was then concentrated, followed by the addition of $H_2O$ (50 mL). It was extracted with EtOAc (3×50 ml) and the combined organic layers dried over anhydrous $Na_2SO_4$. Removal of solvent gave α-acyloxy carbonyls (Ia-v), which were purified by column chromatography over silica gel using pet ether/EtOAc (1/19) as eluent to obtain pure α-acyloxy carbonyls in high purity.

Example 2

2-Oxo-2-phenylethyl 4-nitrobenzoate (IIa)

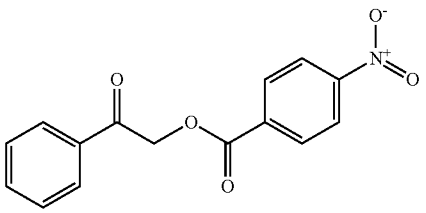 [SMILES: O=C(COC(=O)c1ccc([N+](=O)[O-])cc1)c1ccccc1]

Yield: 92%, colorless solid, Mp: 123-124° C.; IR (Nujol, $cm^{-1}$): 719, 1104, 1229, 1294, 1376, 1462, 1524, 1598, 1696, 1727, 275, 2840, 2923; $^1$H NMR (200 MHz, $CDCl_3$): δ 5.64 (s, 2H), 7.51-7.55 (m, 2H), 7.63-7.65 (m, 1H), 7.97 (d, J=8.5 Hz, 211), 8.33 (s, 4H); $^{13}$C NMR (50 MHz, $CDCl_3$): δ 66.9, 123.4, 127.7, 128.9, 130.9, 133.8, 134.0, 134.7, 150.6, 164.0, 191.0: HRMS (ESI): $[M+H]^+$ calcd for $C_{15}H_{11}NO_5$+H: 286.0715. found: 286.0726.

2-(4-Methylphenyl)-2-oxoethyl 4-nitrobenzoate (IIb)

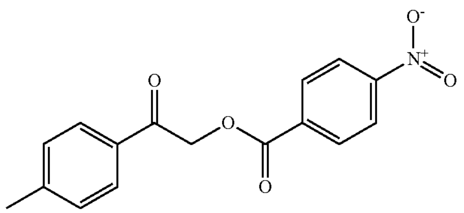 [SMILES: Cc1ccc(C(=O)COC(=O)c2ccc([N+](=O)[O-])cc2)cc1]

Yield: 77%, colorless solid, Mp: 114-115° C.; IR (Nujol, $cm^{-1}$): 713, 1135, 1231, 1289, 1374, 1459, 1525, 1604, 1692, 1725, 2840, 2923; $^1$H NMR (200 MHz, $CDCl_3$): δ 2.46 (s, 3H), 5.62 (s, 2H), 7.32 (d, J=8.1 Hz, 2H), 7.87 (d, J=8.1 Hz, 2H), 8.33 (s, 4H); $^{13}$C NMR (50 MHz, $CDCl_3$): δ 21.8, 66.9, 123.5, 127.8, 129.6, 131.1, 131.5, 134.8, 145.1, 150.7, 164.1, 190.6; HRMS (ESI): $[M+H]^+$ calcd for: $C_{16}H_{13}NO_5$+H: 300.0872. found: 300.0881.

2-(4-Bromophenyl)-2-oxoethyl 4-nitrobenzoate (IIc)

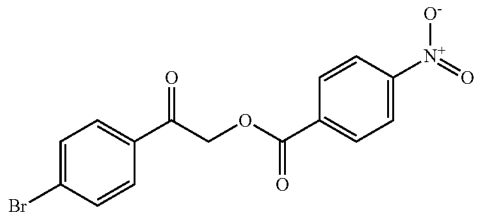 [SMILES: O=C(COC(=O)c1ccc([N+](=O)[O-])cc1)c1ccc(Br)cc1]

Yield: 71%, colorless solid, Mp: 117-118° C.; IR ($CHCl_3$, $cm^{-1}$): 717, 967, 1106, 1124, 1346, 1521, 1701, 1723, 2850, 2920; $^1$H NMR (200 MHz, $CDCl_3$): δ 5.58 (s, 2H), 7.67 (m, J=8.5 Hz, 2H), 7.83 (m, J 8.5 Hz, 2H), 8.32 (s, 4H); $^{13}$C NMR (100 MHz, $CDCl_3$): δ 66.7, 123.6, 129.2, 129.5, 131.1, 132.4, 132.6, 134.6, 150.8, 164.0, 190.0; HRMS (ESI): $[M+H]^+$ calcd for $C_{15}H_{10}BrNNaO_5$+H: 363.9820. found: 363.9834.

2-(4-Fluorophenyl)-2-oxoethyl 4-nitrobenzoate (IId)

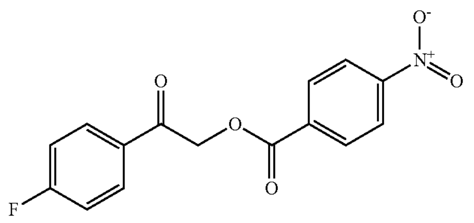 [SMILES: O=C(COC(=O)c1ccc([N+](=O)[O-])cc1)c1ccc(F)cc1]

Yield: 79%, colorless solid, Mp: 117-118° C.; IR ($CHCl_3$, $cm^{-1}$): 717, 871, 1131, 1155, 1231, 1320, 1521, 1595, 1698, 1722, 1746; $^1$H NMR (400 MHz, $CDCl_3$): δ 5.59 (s, 2H), 7.21 (t, J=8.6 Hz, 2H), 8.01 (dd, J=8.6, J=5.0 Hz, 2H), 8.32 (d, J=2.7 Hz, 4H); $^{13}$C NMR (100 MHz, $CDCl_3$): δ 66.7, 116.1, 116.4, 130.5, 130.5, 131.1, 134.6, 150.8, 164.0, 165.0, 167.5, 189.3; HRMS (ESI): $[M+H]^+$ calcd for $C_{15}H_{10}FNO_5$+H: 304.0621. found: 304.0627.

2-(4-Acetoxyphenyl)-2-oxoethyl 4-nitrobenzoate (IIe)

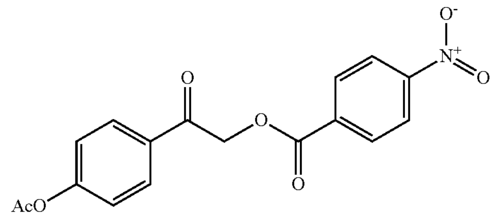 [SMILES: CC(=O)Oc1ccc(C(=O)COC(=O)c2ccc([N+](=O)[O-])cc2)cc1]

Yield: 82%, colorless solid, Mp: 128-129° C.; IR (Nujol, $cm^{-1}$): 716, 1166, 1212, 1294, 1374, 1459, 1525, 1596, 1690, 1717, 1753, 2846, 2917; $^1$H NMR (200 MHz, $CDCl_3$): δ 2.35 (s, 3H), 5.61 (s, 2H), 7.26 (d, J=8.6 Hz, 2H), 8.01 (d, J=8.6 Hz, 2H), 8.32 (s, 4H); $^{13}C$ NMR (100 MHz, $CDCl_3$): δ 21.0, 66.7, 122.2, 123.5, 129.3, 131.0, 131.3, 134.6, 150.6, 155.0, 164.0, 168.4, 189.9; FIRMS (ESI): $[M+H]^+$ calcd for $C_{17}H_{13}NO_7$+H: 344.0770. found: 344.0778.

2-(3,4 Dimethoxyphenyl)-2-oxoethyl 4-nitrobenzoate (IIf)

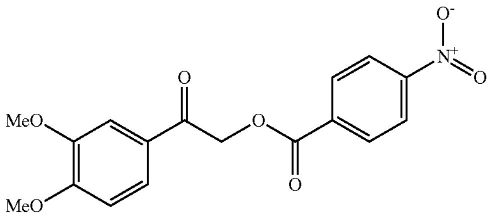 [SMILES: COc1ccc(C(=O)COC(=O)c2ccc([N+](=O)[O-])cc2)cc1OC]

Yield: 74%, colorless solid, Mp: 162-163° C.; IR (Nujol, $cm^{-1}$): 720, 1021, 1131, 1235, 1376, 1460, 1524, 1684, 1725, 2855, 2925; $^1H$ NMR (200 MHz, $CDCl_3$): δ 3.95 (s, 3H), 3.98 (s, 311), 5.60 (s, 2H), 6.92 (d, J=8.3 Hz, 1H), 7.51-7.54 (m, 2H), 8.33 (s, 4H); $^{13}C$ NMR (100 MHz, $CDCl_3$): δ 55.9, 56.0, 66.6, 110.0, 110.1, 122.1, 123.6, 127.1, 131.0, 134.9, 149.5, 150.8, 154.1, 164.1, 189.5; HRMS (ESI): $[M+H]^+$ calcd for $C_{17}H_{15}NO_7$+H: 346.0922. found: 346.0927.

1-Oxo-2,3-dihydro-1H-inden-2-yl 4-nitrobenzoate (IIg)

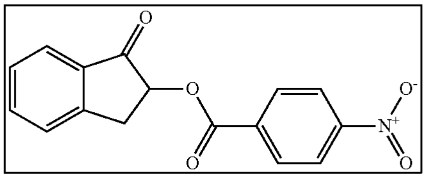 [SMILES: O=C(OC1Cc2ccccc2C1=O)c1ccc([N+](=O)[O-])cc1]

Yield: 72%, colorless solid, Mp: 199-200° C.; IR (Nujol, $cm^{-1}$): 713, 1122, 1273, 1349, 1374, 1522, 1604, 1709, 1722, 2846, 2923; $^1H$ NMR (200 MHz, $CDCl_3$): δ 3.23 (dd, J=17.0, 4.9 Hz, 1H), 3.82 (dd, J=17.0, 8.1 Hz, 1H), 5.70 (dd, J=8.1, 4.9 Hz, 1H), 7.44-7.53 (m, 2H), 7.68 (d, J 7.7 Hz, 1H), 7.86 (d, J 7.7 Hz, 1H), 8.30 (s, 4H); $^{13}C$ NMR (125 MHz, $CDCl_3$): δ 33.4, 75.0, 123.6, 124.7, 126.7, 128.4, 131.1, 134.5, 134.7, 136.1, 150.1, 150.9, 164.1, 199.3; HRMS (ESI): $[M+H]^+$ calcd for: $C_{16}H_{12}NO_5$+H: 298.0715. found: 298.0720.

2-Oxo-1,2-diphenylethyl 4-nitrobenzoate (IIh)

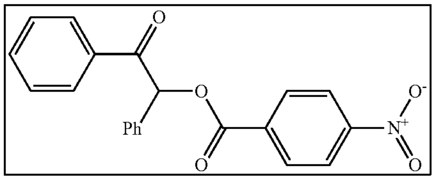 [SMILES: O=C(OC(C(=O)c1ccccc1)c1ccccc1)c1ccc([N+](=O)[O-])cc1]

Yield: 81%, colorless solid, Mp: 114-115° C.; IR (Nujol, $cm^{-1}$): 762, 1097, 1288, 1341, 1374, 1462, 1522, 1692, 1720, 2851, 2923; $^1H$ NMR (200 MHz, $CDCl_3$): δ 7.13 (s, 111), 7.41-7.58 (m, 8H), 7.99 (d, J=7.2 Hz, 2H), 8.28 (s, 4H); $^{13}C$ NMR (50 MHz, $CDCl_3$): δ 78.7, 123.5, 128.7, 128.8, 129.3, 129.7, 131.1, 133.2, 133.6, 134.4, 134.8, 150.7, 164.0, 192.6: HRMS (ESI): $[M+Na]^+$ calcd for: $C_{21}H_{15}NO_5$+Na: 384.0848. found: 384.0853.

1-Oxo-1-phenylpropan-2-yl 4-nitrobenzoate (IIi)

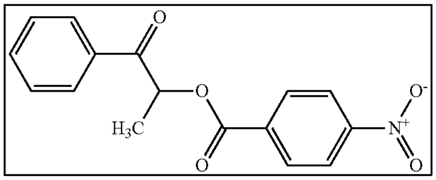 [SMILES: CC(OC(=O)c1ccc([N+](=O)[O-])cc1)C(=O)c1ccccc1]

Yield: 81%, colorless solid, Mp: 119-120° C.; IR (Nujol, $cm^{-1}$): 721, 965, 1122, 1270, 1374, 1462, 1522, 1599, 1692, 1725, 2851, 2923; $^1H$ NMR (200 MHz, $CDCl_3$): δ 1.72 (d, J=6.9 Hz, 3H), 6.23 (q, 0.1=6.9 Hz, 1H), 7.52-7.63 (m, 3H), 7.97-8.01 (m, 211), 8.29-8.30 (m, 4H); $^{13}C$ NMR (100 MHz, $CDCl_3$); δ 17.2, 72.6, 123.4, 128.4, 128.8, 130.9, 133.7, 134.8, 150.6, 163.9, 195.5; HRMS (ESI): $[M+H]^+$ calcd for: $C_{16}H_{13}NO_5$+H: 300.0872. found: 300.0877.

3-((Tert-butyldimethylsilyl)oxy)-1-oxo-1-phenylpropan-2-yl 4-nitro benzoate (IIj)

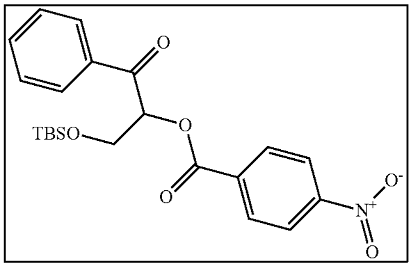 [SMILES: CC(C)(C)[Si](C)(C)OCC(OC(=O)c1ccc([N+](=O)[O-])cc1)C(=O)c1ccccc1]

Yield: 92%, colorless solid, Mp: 77-78° C.; IR (Nujol, $cm^{-1}$): 718, 839, 1270, 1371, 1459, 1530, 1695, 1733, 2851, 2917; $^1H$ NMR (200 MHz, $CDCl_3$): δ 0.00 (s, 3H), 0.02 (s, 3H), 0.82 (s, 9H), 4.18 (d, J=5.1 Hz, 2H), 6.25 (t, J=5.1 Hz, 111), 7.47-7.62 (m, 3H), 8.00-8.04 (m, 2H), 8.29-8.30 (m, 4H); $^{13}C$ NMR (100 MHz, $CDCl_3$): δ −5.4, 18.1, 25.6, 29.7, 62.9, 77.3, 123.5, 128.5, 128.7, 131.0, 133.7, 134.8, 135.2, 150.7, 163.9, 194.4; HRMS (ESI): $[M+H]^+$ calcd for: $C_{22}H_{27}NO_6Si$+H: 430.1686. found: 430.1689.

3-(Benzyloxy)-2-oxopropyl 4-nitrobenzoate (IIk)

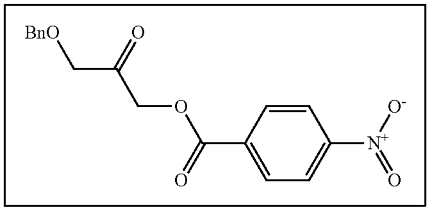 [SMILES: O=C(COCc1ccccc1)COC(=O)c1ccc([N+](=O)[O-])cc1]

Yield: 79%, colorless solid, Mp: 83-84° C.; IR (Nujol, $cm^{-1}$): 718, 1083, 1283, 1374, 1459, 1517, 1722, 1739, 2851, 2823; $^1$H NMR (200 MHz, $CDCl_3$): δ 4.21 (s, 2H), 4.64 (s, 2H), 5.23 (s, 2H), 7.37 (s, 5H), 8.28 (d, J=4.3 Hz, 4H); $^{13}$C NMR (125 MHz, $CDCl_3$): δ 67.8, 73.8, 73.9, 123.5, 127.9, 128.3, 128.6, 130.9, 134.6, 136.5, 150.7, 163.8, 200.8; HRMS (ESI): $[M+Na]^+$ calcd for $C_{17}H_{15}NO_6$+Na: 352.0796. found: 352.0801.

2-Oxooctyl 4-nitrobenzoate (IIl)

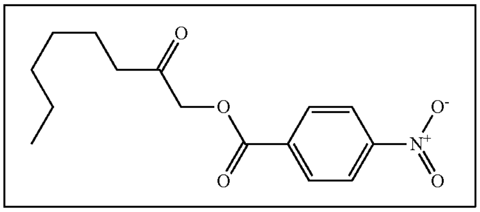 [SMILES: CCCCCCC(=O)COC(=O)c1ccc([N+](=O)[O-])cc1]

Yield: 71%, colorless solid, Mp: 75-76° C.: IR (Nujol, $cm^{-1}$): 717, 1121, 1272, 1352, 1377, 1463, 1536, 1543, 1722, 1733, 2854, 2923; $^1$H NMR (200 MHz, $CDCl_3$): δ 0.87-0.93 (m, 3H), 1.26-1.31 (br. s, 6H), 1.67-1.70 (m, 2H), 2.49 (t, J=7.3 Hz, 2H), 4.94 (s, 2H), 8.24-8.35 (m, 4H); $^{13}$C NMR (125 MHz, $CDCl_3$): δ 13.9, 22.4, 23.2, 28.7, 31.5, 38.7, 68.7, 123.5, 130.9, 134.6, 150.7, 163.8, 202.4: HRMS (ESI): $[M+H]^+$ calcd for $C_{15}H_{19}NO_5$+H: 294.1341. found: 294.1347.

2-Oxodecyl 4-nitrobenzoate (IIm)

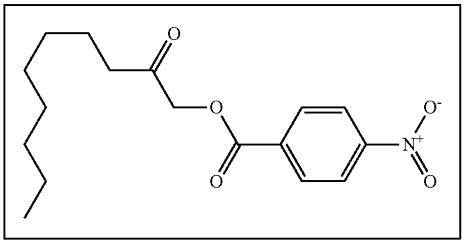 [SMILES: CCCCCCCCC(=O)COC(=O)c1ccc([N+](=O)[O-])cc1]

Yield: 76%, colorless solid, Mp: 76-77° C.; IR (Nujol, $cm^{-1}$): 713, 1119, 1270, 1374, 1459, 1541, 1610, 1717, 1736, 2857, 2928; $^1$H NMR (200 MHz, $CDCl_3$): δ 0.85-0.92 (m, 3H), 1.29 (br. s., 10H), 1.66 (t, J=7.2 Hz, 2H), 2.49 (t, J=7.2 Hz, 2H), 4.94 (s, 2H), 8.24-8.35 (m, 4H); $^{13}$C NMR (50 MHz, $CDCl_3$): δ 14.0, 22.5, 23.2, 29.0, 29.0, 29.2, 31.7, 38.6, 68.6, 123.4, 130.8, 134.6, 150.6, 163.7, 202.2; HRMS (ESI): $[M+H]^+$ calcd for $C_{17}H_{23}NO_5$+H: 322.1654. found: 322.1656.

2-Oxo-4-phenylbutyl 4-nitrobenzoate (IIn)

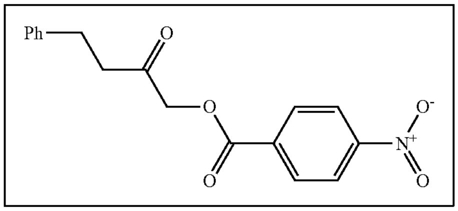 [SMILES: O=C(CCc1ccccc1)COC(=O)c1ccc([N+](=O)[O-])cc1]

Yield: 74%, colorless solid, Mp: 112-113° C.; IR (Nujol, $cm^{-1}$): 724, 1089, 1131, 1273, 1347, 1377, 1462, 1523, 1600, 1718, 1732, 2855, 2926; $^1$H NMR (200 MHz, $CDCl_3$): δ 2.79-2.87 (m, 211), 2.95-3.03 (m, 211), 4.91 (s, 2H), 7.21-7.31 (m, 511), 8.27-8.34 (m, 4H); $^{13}$C NMR (50 MHz, $CDCl_3$): δ 29.2, 40.4, 68.8, 123.6, 126.4, 128.2, 128.6, 131.0, 138.0, 140.2, 150.8, 163.9, 201.7; HRMS $[M+Na]^+$ calcd for: $C_{17}H_{15}NO_5$+Na: 336.0848. found: 336.0856.

2-Ethoxy-2-oxoethyl 4-nitrobenzoate (IIo)

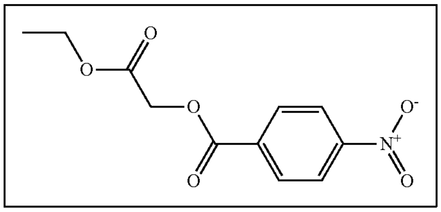 [SMILES: CCOC(=O)COC(=O)c1ccc([N+](=O)[O-])cc1]

Yield: 78%, yellow liquid; IR (neat, $cm^{-1}$): 2926, 2983, 1759, 1738, 1732, 1608, 1531, 1349, 1285, 1213, 1121, 1018, 857, 718; $^1$H NMR (200 MHz, $CDCl_3$): δ 1.33 (t, J=7.1 Hz, 3H), 4.28 (q, J=7.1 Hz, 2H), 4.89 (s, 2H), 8.25-8.36 (m, 4H); $^{13}$C NMR (50 MHz, $CDCl_3$): δ 14.1, 61.5, 123.5, 131.0, 134.5, 150.8, 163.9, 166.9; HRMS (ESI): $[M+Na]^+$ calcd for $C_{11}H_{11}NO_6$+Na: 276.0484. found: 276.0446.

2-Oxotetrahydro-2H-pyran-3-yl 4-nitrobenzoate (IIp)

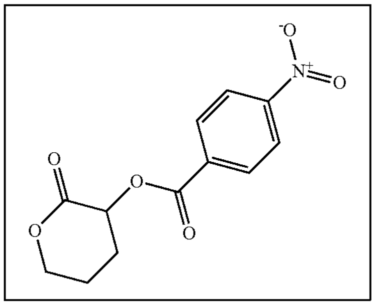

Yield: 69%, colorless solid, Mp: 136-137° C.; IR (Nujol, $cm^{-1}$): 718, 1124, 1273, 1377, 1456, 1511, 1602, 1725, 1753, 2857, 2912; $^1$H NMR (200 MHz, $CDCl_3$): δ 2.14-2.20 (m, 3H), 2.51-2.76 (m, 1H), 4.43-4.49 (m, 2H), 5.61-5.67 (m, 1H), 8.25-8.35 (m, 4H); $^{13}$C NMR (50 MHz, $CDCl_3$): δ 21.3, 24.8, 68.2, 68.2, 123.5, 131.0, 134.5, 150.7, 163.4, 168.1; HRMS (ESI): $[M+H]^+$ calcd for $C_{12}H_{11}NO_6$+H: 266.0664. found: 266.0663.

2-(Methoxy)-2-oxo-1-phenylethyl 4-nitrobenzoate (IIq)

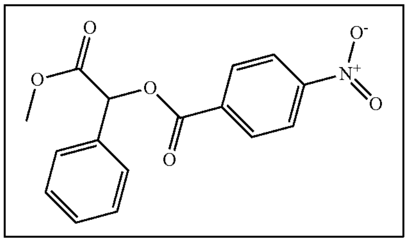 [SMILES: COC(=O)C(OC(=O)c1ccc([N+](=O)[O-])cc1)c1ccccc1]

Yield: 72%, yellow liquid; IR ($CHCl_3$, $cm^{-1}$): 718, 1101, 1167, 1269, 1346, 1368, 1508, 1527, 1606, 1731, 1760; $^1H$ NMR (500 MHz, $CDCl_3$): δ 3.80 (s, 3H), 6.20 (s, 1H), 7.47-7.48 (m, 3H), 7.59-7.60 (m, 2H), 8.32 (s, 4H); $^{13}C$ NMR (125 MHz, $CDCl_3$): δ 52.6, 75.4, 123.5, 127.7, 128.9, 129.5, 131.0, 133.3, 134.5, 150.8, 163.7, 168.5; HRMS (ESI): $[M+Na]^+$ calcd for $C_{16}H_{13}NO_6$+Na: 338.0641. found: 338.0649.

2-Oxo-2-phenylethyl benzoate (IIr)

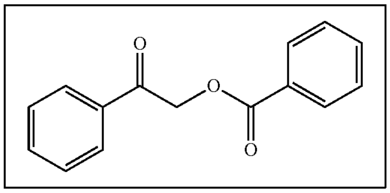 [SMILES: O=C(COC(=O)c1ccccc1)c1ccccc1]

Yield: 68%, colorless solid, Mp: 119-120° C.; IR (Nujol, $cm^{-1}$): 705, 1015, 1374, 1459, 1596, 1714, 1750, 2851, 2923; $^1H$ NMR (200 MHz, $CDCl_3$): δ 5.58 (s, 211), 7.48-7.61 (m, 6H), 7.97-8.00 (m, 2H), 8.13-8.17 (m, 2H); $^{13}C$ NMR (50 MHz, $CDCl_3$): δ 66.2, 127.6, 128.2, 128.73, 129.8, 130.1, 133.1, 133.6, 134.1, 165.7, 191.6; HRMS (ESI): $[M+Na]^+$ calcd for $C_{15}H_{12}O_3$+Na: 263.0683. found: 263.0692.

2-Oxo-2-phenylethyl 3-methylbenzoate (IIs)

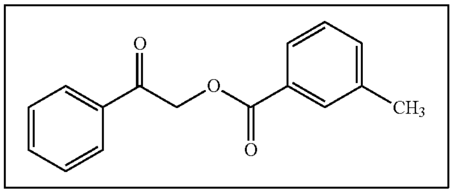 [SMILES: Cc1cccc(C(=O)OCC(=O)c2ccccc2)c1]

Yield: 81%, colorless solid, Mp: 94-95° C.; IR (Nujol, cm): 743, 814, 957, 1083, 1198, 1369, 1451, 1585, 1684, 1714, 2857, 2917; $^1H$ NMR (200 MHz, $CDCl_3$): δ 2.38 (s, 3H), 5.52 (s, 2H), 7.31-7.48 (m, 5H), 7.90-7.95 (m, 4H); $^{13}C$ NMR (100 MHz, $CDCl_3$): δ 21.1, 66.2, 127.0, 127.6, 128.2 128.7, 129.2, 130.3, 133.6, 133.9, 134.1, 137.9, 165.8, 191.7; HRMS (ESI): $[M+Na]^+$ calcd for $C_{16}H_{14}O_3$+Na: 277.0840. found: 277.0848.

2-Oxo-2-phenylethyl 4-bromobenzoate (IIt)

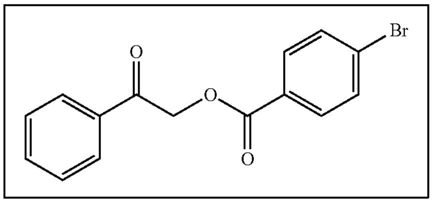 [SMILES: O=C(COC(=O)c1ccc(Br)cc1)c1ccccc1]

Yield: 78%, colorless solid, Mp: 84-85° C.; IR (Nujol, $cm^{-1}$): 766, 1012, 1126, 1327, 1588, 1643, 1711, 1732, 2923, 295'6; $^1H$ NMR (200 MHz, $CDCl_3$): δ 5.57 (s, 211), 7.44-7.64 (m, 5H), 7.94-8.03 (m, 4H); $^{13}C$ NMR (50 MHz, $CDCl_3$): δ 66.4, 127.7, 128.3, 128.4, 128.8, 131.4, 131.7, 133.8, 134.1, 165.0, 191.4: HRMS (ESI): $[M+Na]^+$ calcd for $C_{15}H_{11}BrO_3$+Na: 340.9789. found: 340.9799.

2-Oxo-2-phenylethyl 4-chlorobenzoate (IIu)

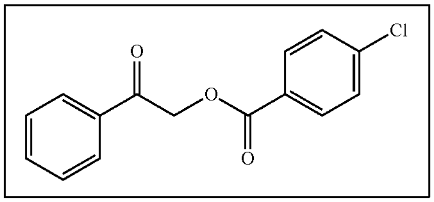 [SMILES: O=C(COC(=O)c1ccc(Cl)cc1)c1ccccc1]

Yield: 75%, colorless solid, Mp: 127-128° C.; IR (Nujol, $cm^{-1}$): 753, 1091, 1226, 1273, 1376, 1456, 1595, 1697, 1726, 2724, 2857, 2926; $^1H$ NMR (500 MHz, $CDCl_3$): δ 5.58 (s, 2H) 7.44-7.56 (m, 5H), 7.97 (d, J=7.3 Hz, 2H) 8.07 8.11 (d, J=7.3 Hz, 2H); $^{13}C$ NMR (125 MHz, $CDCl_3$): δ 66.5, 77.0, 127.8, 128.6, 128.8, 128.9, 131.3, 133.9, 134.2, 139.8, 165.0, 191.6; HRMS (ESI): $[M+Na]^+$ calcd for $C_{15}H_{11}ClO_3$+Na: 297.0294. found: 297.0294.

2-Oxo-2-phenylethyl nicotinate (IIv)

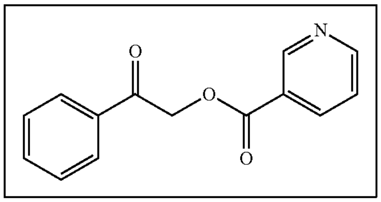 [SMILES: O=C(COC(=O)c1cccnc1)c1ccccc1]

Yield: 73%, colorless solid, Mp: 64-65° C.: IR ($CHCl_3$, $cm^{-1}$): 753, 1076, 1342, 1463, 1591, 1650, 1695, 1726, 2854, 2870, 2923; $^1H$ NMR (400 MHz, $CDCl_3$); δ 5.61 (s, 214), 7.44 (dd, J=7.6, 4.9 Hz, 1H) 7.50-7.54 (m, 2H), 7.62-7.64 (m, 1H), 7.97 (d, J=7.5 Hz, 2H), 8.40 (d, J=7.7 Hz, 1H), 8.82 (br. s, 1H), 9.33 (br. s, 1H); $^{13}C$ NMR (100 MHz, $CDCl_3$) δ 66.6, 123.3, 125.6, 127.8, 128.9, 134.0, 134.1, 137.4, 151.2, 153.7, 164.6, 191.1; HRMS (ESI): $[M+Na]^+$ calcd for $C_{14}H_{11}NO_3$+Na: 264.0637. found: 264.0648.

Advantages of the Invention

A new catalytic regio selective method for the preparation of acyloxy carbonyl products in preparative yield from a variety of olefins including aromatic, aliphatic and electron rich at ambient conditions is disclosed. This method is simple, milder and the reagents used are cheap and easy to handle. The process avoids metal catalysts.

The invention claimed is:

1. A single-step, one pot process for the preparation of an α-acyloxy carbonyl compound of general formula (I);

General formula (I)

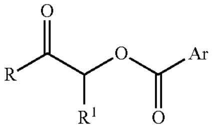

wherein R is selected from H, alkyl, aryl, Bn; $R^1$ is selected from H, alkyl, substituted aryl, unsubstituted aryl, —$CH_2$OTBS (TBS=Tertiary butyl silyl), —$CH_2$OBn, —OR, OMOM (Methoxy methelene); Ar is selected from unsubstituted/substituted phenyl group or pyridine group; R and $R^1$ optionally can combine to form a ring structure containing 3 to 6 carbon atoms and may optionally contain a heteroatom;

comprising the steps of: reacting alkene of formula (II) with an aldehyde of formula (III)

(II)

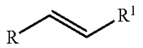

(III)

Ar—CHO in the presence of a N-Heterocyclic carbene catalyst (NHC) selected from

IVa

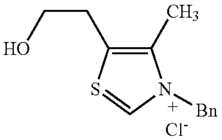

IVb, IVc

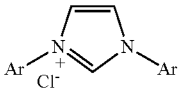

IVd

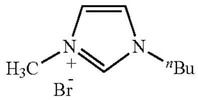

IVe

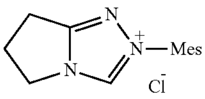

IVf

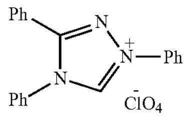

wherein for IVb, Ar=2,4,6-$(CH_3)_3C_6H_2$; for IVc, Ar=2, 6-$iPr_2C_6H_3$, a halogen source, tri-ethyl amine and a solvent in oxygen atmosphere at a temperature in the range of 15-30° C. by stirring for a period in the range of 10-50 hours to obtain a compound of general formula (I); wherein R is selected from H, alkyl, aryl, Bn; $R^1$ is selected from H, alkyl, substituted aryl, unsubstituted aryl —$CH_2$OTBS (TBS=Tertiary butyl silyl), —$CH_2$OBn, —OR, OMOM (Methoxy methelene); Ar is selected from unsubstituted/substituted phenyl group or pyridine group.

2. The process as claimed in claim 1, wherein N-Heterocyclic carbene catalyst is Iva[-IVf, preferably Iva.]

IVa

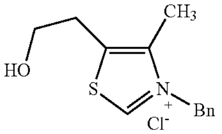

3. The process as claimed in claim 1, wherein halogen source is selected from the group consisting of N-bromo succinamide (NBS), N-iodo succinamide NIS or N-chloro succinamide NCS.

4. The process as claimed in claim 1, wherein solvent used is di-methyl sulfoxide (DMSO).

5. The process as claimed in claim 1, wherein the N-Heterocyclic carbene catalyst is IVa and the yield of the compound of general formula (I) is in the range of 70 to 92%.

6. The process according to claim 1, wherein representative compound of general formula (I) are:

2-Oxo-2-phenylethyl 4-nitrobenzoate (1a);
2-(4-Methylphenyl)-2-oxoethyl 4-nitrobenzoate (1b);
2-(4-Bromophenyl)-2-oxoethyl 4-nitrobenzoate (Ic);
2-(4-Fluorophenyl)-2-oxoethyl 4-nitrobenzoate (Id);
2-(4-Acetoxyphenyl)-2-oxoethyl 4-nitrobenzoate (Ie);
2-(3,4 Dimethoxyphenyl)-2-oxoethyl 4-nitrobenzoate (If);
1-Oxo-2,3-dihydro-1H-inden-2-yl 4-nitrobenzoate (Ig);
2-Oxo-1,2-diphenylethyl 4-nitrobenzoate (Ih);
1-Oxo-1-phenylpropan-2-yl 4-nitrobenzoate (Ii);
2-((Tert-butyldimethylsilyl)oxy)-1-oxo-1-phenylpropan-2-yl 4-nitro benzoate (Ij);
3-(Benzyloxy)-2-oxopropyl 4-nitrobenzoate (Ik);
3-Oxooctyl 4-nitrobenzoate (Il);
2-Oxodecyl 4-nitrobenzoate (Im);
2-Oxo-4-phenylbutyl 4-nitrobenzoate (In);
2-Ethoxy-2-oxoethyl 4-nitrobenzoate (Io);
2-Oxotetrahydro-2H-pyran-3-yl 4-nitrobenzoate (Ip);
2-(Methoxy)-2-oxo-1-phenylethyl 4-nitrobenzoate (Iq);
2-Oxo-2-phenylethyl benzoate (Ir);
2-Oxo-2-phenylethyl 3-methylbenzoate (Is);
2-Oxo-2-phenylethyl 4-bromobenzoate (It);
2-Oxo-2-phenylethyl 4-chlorobenzoate (Iu);
2-Oxo-2-phenylethyl nicotinate (Iv).

7. The process as claimed in claim 1, wherein halogen source is N-bromo succinamide (NBS).

* * * * *